United States Patent [19]

Seshimoto et al.

[11] Patent Number: 4,613,420

[45] Date of Patent: Sep. 23, 1986

[54] APPARATUS FOR MEASURING IONIC ACTIVITY

[75] Inventors: Osamu Seshimoto; Yoshio Saito; Teruaki Koizumi; Masaaki Terashima, all of Asaka, Japan

[73] Assignee: Fuji Photo Film Co., Ltd., Kanagawa, Japan

[21] Appl. No.: 694,220

[22] Filed: Jan. 24, 1985

[30] Foreign Application Priority Data

Jan. 25, 1984 [JP] Japan .................................. 59-12795

[51] Int. Cl.⁴ ............................................. G01N 27/28
[52] U.S. Cl. .................................... 204/412; 204/407; 204/416
[58] Field of Search ............... 204/416, 407, 409, 411, 204/412; 422/64, 65, 68; 222/214

[56] References Cited

U.S. PATENT DOCUMENTS

| | | | |
|---|---|---|---|
| 3,679,331 | 7/1972 | Kushner | 222/214 X |
| 4,257,862 | 3/1981 | Schnipelsky et al. | 204/400 |
| 4,269,803 | 5/1981 | Jessop | 422/65 X |
| 4,446,993 | 5/1984 | Tokorozawa | 222/214 |

Primary Examiner—G. L. Kaplan
Attorney, Agent, or Firm—Toren, McGeady, Stanger, Goldberg & Kiel

[57] ABSTRACT

An apparatus for measuring ionic activity has a nozzle connected to a reservoir containing a reference solution. The reference solution is pumped up from the reservoir without coming into contact with air, so as to be quantitatively dripped through the nozzle when a slide-type ionic activity measuring device is located at a position below the nozzle. After the reference and sample solutions are spotted on the ionic activity measuring device, at least one pair of probes comes into contact with the device so as to measure potential difference corresponding to ionic activity difference of at least one ion between the reference and sample solutions.

5 Claims, 8 Drawing Figures

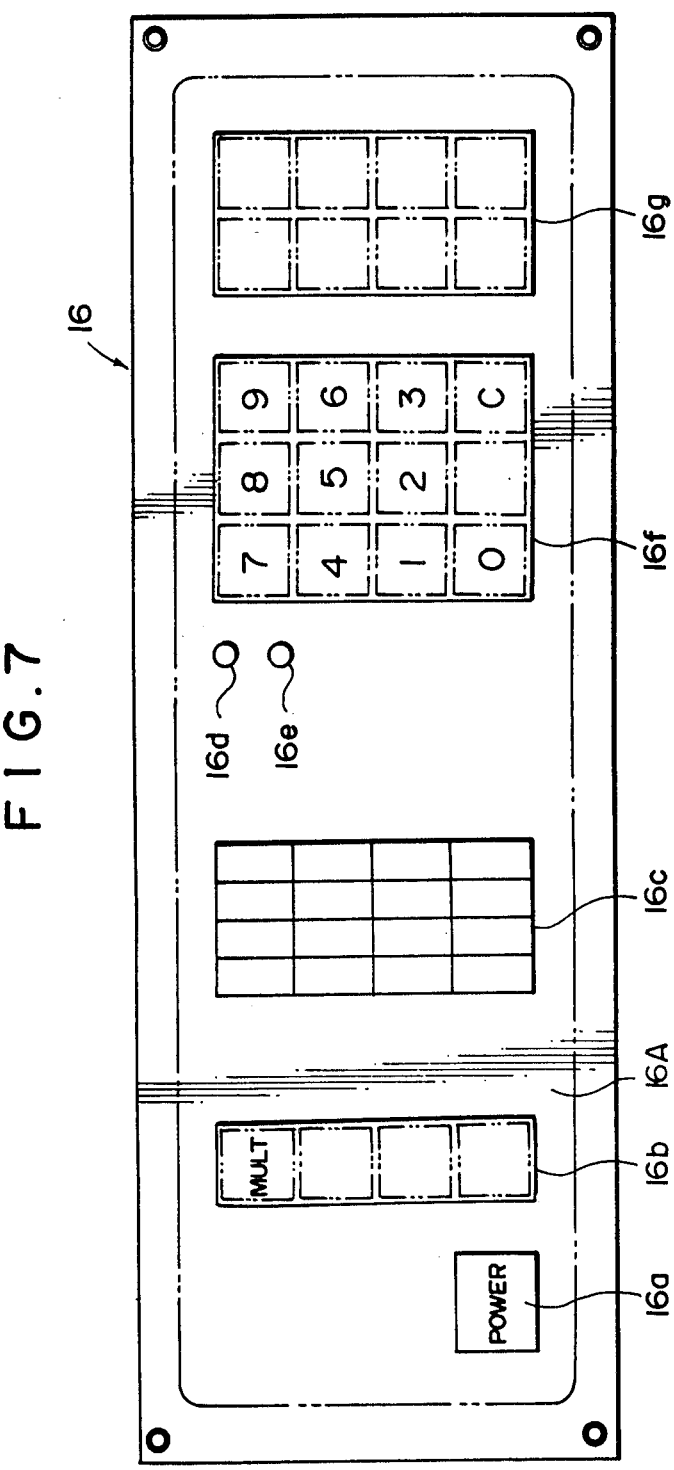

APPARATUS FOR MEASURING IONIC ACTIVITY

BACKGROUND OF THE INVENTION

1. Field of the Invention

This invention relates to an apparatus for measuring ionic activity of electrolytes contained in aqueous liquid samples such as body fluids. More particularly, this invention relates to a novel potentiometric electrolyte analyzer in which a slide-type ionic activity measuring device having ion-selective electrodes is transferred from a spotting section to a discharging section by way of a measuring section.

2. Description of the Prior Art

Measurement of ionic activity of an electrolyte ion, for example $Na^+$, $K^+$, $Cl^-$, $Ca^{2+}$, $HCO_3^-$ or $CO_3^{2-}$, contained in such body fluids as whole blood, blood plasma, blood serum, and urine, has significant importance in clinical chemistry tests. For this measurement, an ionic activity measuring apparatus, i.e. a so-called electrolyte analyzer, has been used. Such techniques as flame analysis, coulometry and potentiometry are known for use in said analyzer.

In potentiometric measurement of ionic activity, an ionic activity measuring device having ion-selective electrodes is used. As such a device, a dry type device having film-like ion-selective electrodes has been disclosed, for example, in U.S. Pat. Nos. 4,053,381 and 4,437,970.

The basic structure of this ionic activity measuring device is that of a slide comprising at least one pair of solid state electrodes each of which has an ion-selective outermost layer and a porous bridge which can promote capillary action between two such ion-selective layers. The ionic activity of a specific ion contained in a sample solution can be determined by spotting a reference solution on one of the ion-selective layers and a sample solution on the other and then measuring the potential difference between the electrodes.

Accordingly, spotting of reference and sample solutions as well as measurement of potential difference must be conducted in an ionic activity analyzer in which this slide type device is used.

The conventional analyzer for this purpose is not only large in size but also has the following drawbacks in the structure of the means for spotting the reference solution. In the conventional analyzer since the reference solution is pumped up from reservoir by a nozzle and then spotted on the slide by the same nozzle, the surface of the reference solution comes into contact with air, causing a change in the concentration thereof. Also, since the nozzle has to be sufficiently deep into the solution so it is not exposed by a lowering of the liquid level, the volume of liquid which adheres to the wall of the nozzle on suction changes at each suction so that the spotting volume is not constant.

In such measurement of the ionic activity, the change in concentration of the solution, which causes errors in the measurement, becomes a particularly serious problem in practice.

SUMMARY OF THE INVENTION

It is thus an object of the present invention to provide an apparatus for measuring ionic activity having a means for liquid-spotting which can provide a constant supply of a reference solution.

It is a specific object of the present invention to provide an apparatus for measuring ionic activity having a means for liquid-spotting by which a reference solution is supplied without coming into contact with air, so that the concentration thereof is not changed.

It is another specific object of the present invention to provide an apparatus for measuring ionic activity having a means for liquid-spotting in which a predetermined constant volume of a reference solution is discharged through a nozzle without adhering to the wall thereof.

The apparatus for measuring ionic activity in accordance with the present invention is characterized in that it has a nozzle connected to a reservoir of a reference solution through which a predetermined constant volume of the reference solution is dripped.

To drip a predetermined constant volume of the reference solution through the nozzle, such means as a peristaltic pump that can quantitatively transfer a micro volume of liquid is used. Also, a drip dispenser with reservoir can be used.

That is, as the means for liquid-spotting of the apparatus in accordance with the present invention, there is adapted a structure in which a reference solution in a reservoir is quantitatively dripped through a nozzle.

BRIEF DESCRIPTION OF THE DRAWINGS

FIG. 7 is a front view of an example of an operation and display section for use in the apparatus in accordance with the present invention.

DESCRIPTION OF THE PREFERRED EMBODIMENTS

The preferred embodiments of the present invention will hereinbelow be described with reference to the accompanying drawings.

Figure 1:
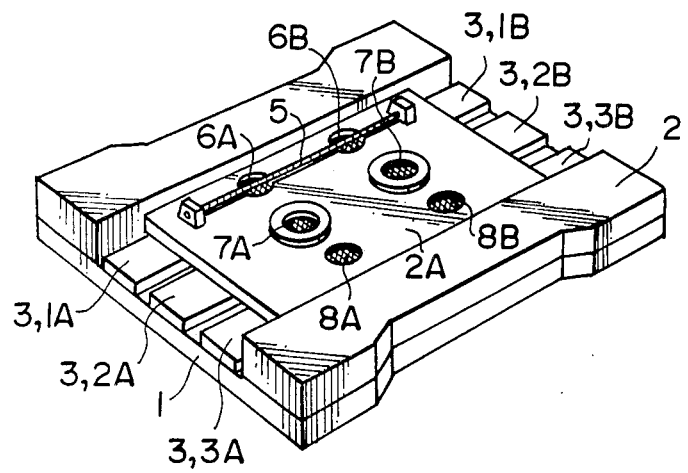
FIG. 1 is a perspective view of an embodiment of a potentiometric ionic activity measuring device to which the apparatus in accordance with the present invention is applicable.

FIG. 1 is a perspective view of an example of a slide-type ionic activity measuring device or article (i.e. a slide) to which the apparatus in accordance with the present invention is applicable. The slide here comprises a lower slide frame 1, an upper slide frame 2, and three pairs of ion-selective electrodes 3.1A,3.1B; 3.2A,3.2B; and 3.3A,3.3B, each of said pairs having an ion-selective outermost layer (not shown) and being disposed between said lower and upper slide frames 1 and 2. Three pairs of through holes 6A,6B; 7A,7B; and 8A,8B are formed in the center portion 2A of the upper slide frame 2. These through holes are functionally divided into a pair of apertures for liquid-spotting 7A and 7B, and two pairs of vent apertures 6A,6B; and 8A,8B. A porous bridge (spun yarn or thread bridge) 5 which can promote capillary action is disposed on the vent apertures 6A and 6B. The ends of the bridge 5 are fixed on the upper slide frame 2. Although not shown in the drawing, first and second porous members for liquid distribution (made of such material as cotton bandage, cotton gauze, or filter paper) are disposed between the ion-selective layers of the first set of ion-selective electrodes 3.1A, 3.2A, and 3.3A and the first set of through holes 6A, 7A and 8A; and between the ion-selective layers of the second set of ion-selective electrodes 3.1B, 3.2B, and 3.3B and the second set of through holes 6B, 7B and 8B.

Each pair of said ion-selective electrodes may have a different ion-selectivity, for example, the electrodes 3.1A and 3.1B for $Na^+$; 3.2A and 3.2B for $K^+$; and 3.3A and 3.3B for $Cl^{31}$. In this case, for example, one or more droplets of a reference solution containing $Na^+$, $K^+$, and $Cl^-$ of a known ionic activity is spotted on the aperture for liquid-spotting 7A and one or more droplets of a sample solution (e.g. whole blood or blood serum) is spotted on the aperture for liquid-spotting 7B so as to determine the ionic activity of said ions. Said reference and sample solutions diffuse through the porous members for liquid distribution so as to hemispherically rise from the vent apertures 6A and 6B, respectively, and then penetrate the porous bridge 5 so that their interfaces meet within said bridge, thus forming an electrical conduction therebetween. At that point, a pair of probes are brought into contact with each pair of terminal portions of said pairs of electrodes, so that the potential difference between each pair of said electrodes is measured (i.e. between 3.1A and 3.1B, 3.2A and 3.2B, and 3.3A and 3.3B). The term "potential difference" as used herein refers to difference in electro-motive force between a pair of ion-selective electrodes. The ionic activity of each of the ions is determined from thus measured potential difference with reference to its corresponding calibration curve.

The foregoing type of slide which can simultaneously measure the ionic activity of different ions is fully described in U.S. Pat. No. 4,437,970.

Figure 2:
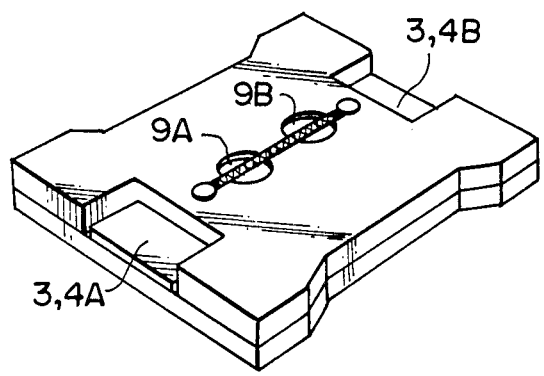
FIG. 2 is a perspective view of another example of a potentiometric ionic activity measuring device.

FIG. 2 shows an example of an ionic activity measuring device in which the ionic activity of only one predetermined ion is measurable. This slide has a pair of apertures for liquid-spotting 9A and 9B, and a pair of ion-selective electrodes 3.4A and 3.4B corresponding thereto.

Figure 3:
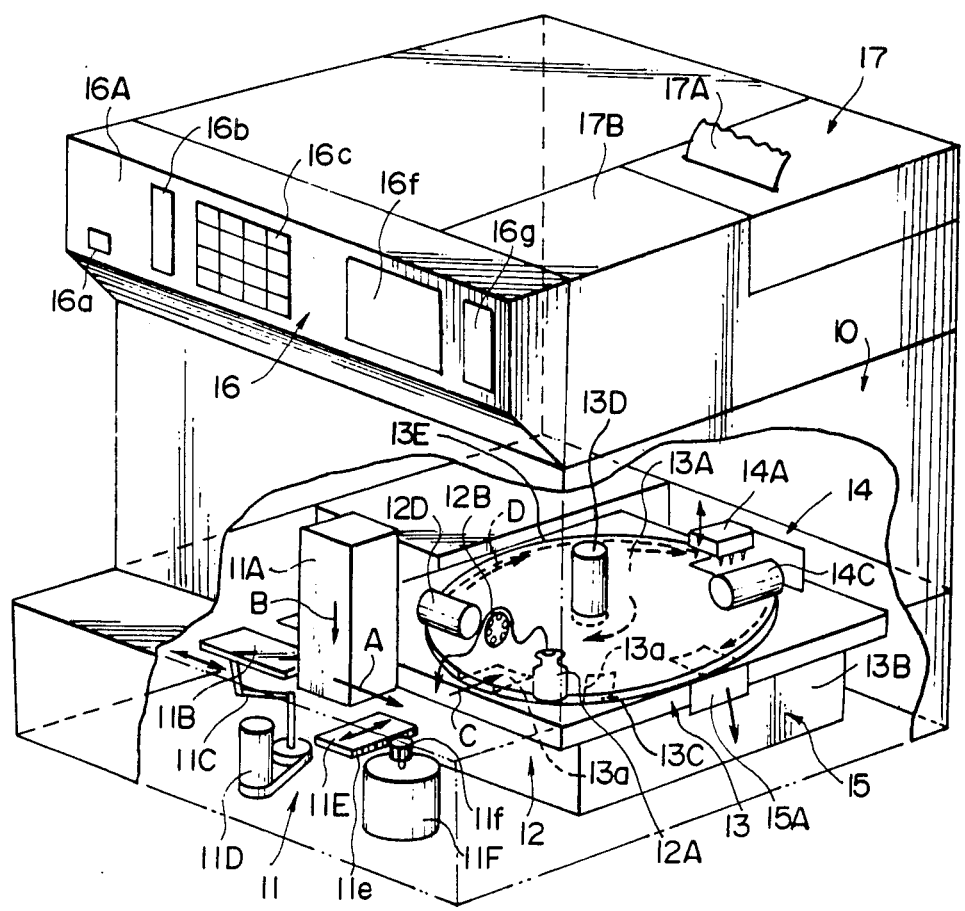
FIG. 3 is a schematic perspective view of an embodiment of the apparatus in accordance with the present invention.

FIG. 3 shows an embodiment of the apparatus for measuring ionic activity in accordance with the present invention. The present invention will hereinbelow be described in detail with reference to this embodiment.

The apparatus represented by this drawing is contained in a housing 10 and consists of a slide supplying section 11, a spotting section 12, a thermostatic means 13, a measuring section 14, a discharging section 15, an operation and display section 16, and a printer 17.

The slide supplying section 11 comprises a slide holder 11A which contains a stack of slides, a slide pushing member 11B which pushes out one slide at a time from the lower end of said holder 11A, and a crank member 11C driven by a motor 11D which reciprocates said pushing member 11B. When the lowest slide is pushed out by the pushing member 11B in the direction indicated by arrow A, the stack of slides within the slide holder 11A descends in the direction of arrow B. The pushing member 11B enters the slide holder 11A through an opening formed on a side face of the lower end thereof so as to push out a slide, and then exits from the holder 11A, allowing the next slide to descend to the lowermost position in the holder 11A.

The slide pushed out of the holder 11A is thrust in the direction indicated by arrow C by charging means 11E which has a rack 11e which engages with a pinion 11f fixed on the shaft of a motor 11F and which is reciprocated by the rotation of said motor 11F. The slide thrust by the charging means 11E is pushed into one of the slide receiving portions 13a formed on the periphery of a disc-like turret 13A.

At a certain stage before, during (i.e. at a position where an intermittently supplied slide stops), and after the insertion of the slide, one or more droplets of the reference solution from a reservoir 12A is spotted on the slide by means of a peristaltic pump 12B.

Figure 4:
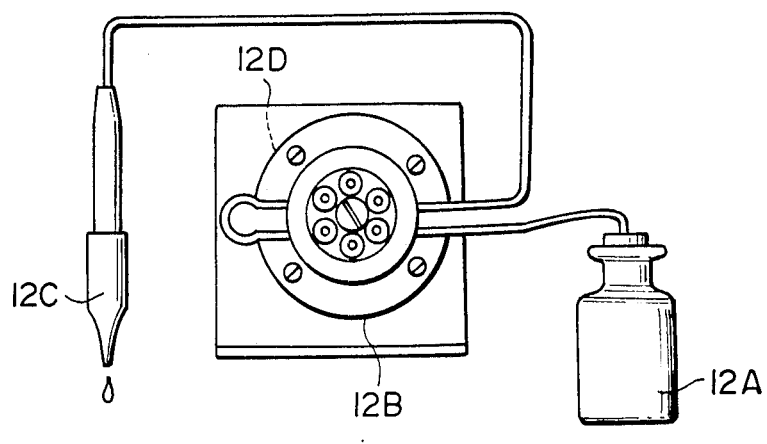
FIG. 4 is a schematic view of an example of a peristaltic pump which can be used in the spotting section of the apparatus in accordance with the present invention.

An example of a device to be used for the spotting of the reference solution is shown in detail in FIG. 4. The intake of the peristaltic pump 12B is connected to the reservoir 12A of the reference solution and the outlet to a nozzle 12C, so that said reference solution is fed, droplet by droplet, from the nozzle 12C, by means of a motor 12D, onto one of the pair of apertures for liquid-spotting of the slide located below the nozzle 12C. Such a peristaltic pump is preferably used for the apparatus in accordance with the present invention since the reference solution is fed only in one direction so that it can be supplied at a constant volume and concentration.

Figure 5:
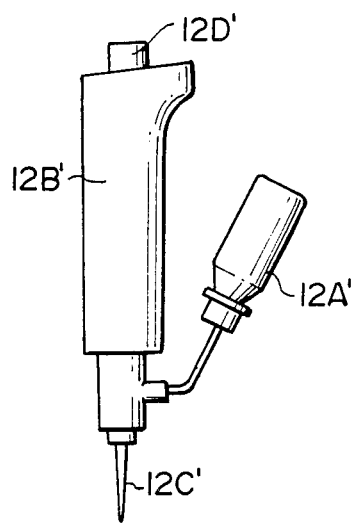
FIG. 5 is a front view of an example of a drip dispenser which can be used in said spotting section.

However, other types of spotting means, including the drip dispenser with reservoir shown in FIG. 5, can also be used. The dispenser represented by this drawing comprises a reservoir 12A', a discharging means 12B', a nozzle 12C' and a button 12D'. Each time the button 12D' is pressed, a droplet of the liquid contained in the reservoir 12A' is discharged from the nozzle 12C'.

By using one of the spotting means described, a constant volume of the reference solution is deposited on one aperture for liquid-spotting (e.g. 7A of FIG. 1 or 9A of FIG. 2) of each slide.

Preferably at nearly the same time, one or more droplets of a sample solution is manually or automatically spotted on the other aperture for liquid-spotting (e.g. 7B of FIG. 1 or 9B of FIG. 2) of the same slide, using any of the known techniques.

The slide which has been thus spotted is conveyed in the direction of arrow D by the rotation of said turret 13A.

The turret 13A is rotatably disposed upon a thermostatic plate 13C which is fixed to a heater (or a thermocooler) 13B, and is intermittently rotated in the direction of arrow D by means of a motor 13D. The angle of this intermittent rotation is equal to the angular distance between one slide receiving portion 13a and the next, said slide receiving portions being disposed equidistantly. A guiding wall having a height not less than the thickness of the turret 13A is formed around the rim of said turret 13A so as to prevent the slides from falling out from the slide receiving portions 13a due to the rotation of said turret 13A.

In order to prevent the reference and sample solutions spotted on the slides from evaporating water as well as to sufficiently maintain the thermostatic effect obtained by the thermostatic plate 13C, a cover (not shown) which shields the upper faces of the slides from the ambient atmosphere is disposed upon the turret 13A. Naturally, this cover has an opening at the measuring section, which will be described hereinbelow, and at the spotting section in case the slide is inserted into the slide receiving portion 13a in the turret 13A prior to the spotting, so that necessary operations can be conducted with the cover in place.

Figure 6A:
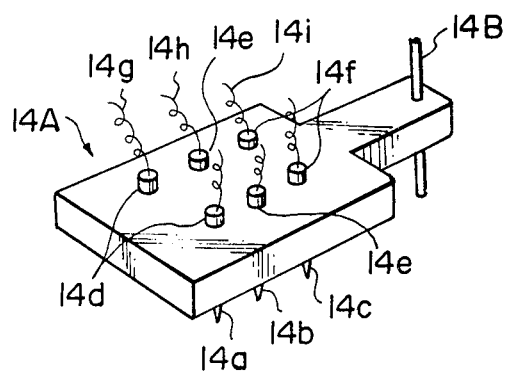
FIG. 6A is a perspective view of an example of a probe assembly used in the apparatus of the present invention.
Figure 6B:
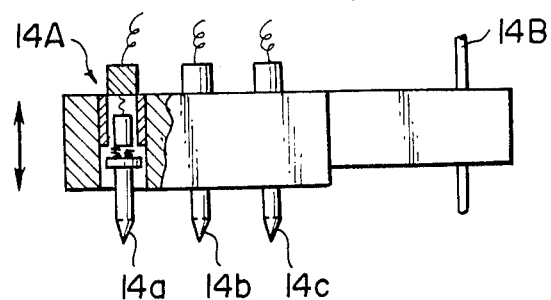
FIG. 6B is a partial sectional side view of said probe assembly.

Within the rotation area of the turret 13A, a vertically movable probe assembly 14A for measuring potential difference is disposed. As shown in FIGS. 6A and 6B, the aforesaid measuring section 14 comprises the probe assembly 14A having, if the slide shown in FIG. 1 is used, six needle-like terminals 14a, 14b, 14c, . . . which are resiliently projected, and lead wires 14g, 14h, and 14i for outputting the potential difference from contacts 14d, 14e, and 14f of said terminals to a measuring circuit (not shown); and a guide 14B to which said probe assembly 14A is connected so as to be vertically movable. This probe assembly 14 is vertically moved by means of a known mechanism (not shown) which is driven by a motor 14C.

Though in accordance with the foregoing embodiment the slide is conveyed with its apertures for liquid-spotting facing up, the slide can also be conveyed with said apertures facing down. In the latter case, the probe assembly may be moved upwardly from below with its probes projecting up so as to come into contact with the terminals of said slide.

The turret 13A conveys the slide, by way of the measuring section 14, to the discharging section 15 which consists of a discharging chute 15A formed in the thermostatic plate 13C. Since the slide receiving portion 13a of the turret 13A consists of a cutout, the slide received in the cutout is slidably shifted on the thermostatic plate 13C together with the rotation of said turret 13A so as to be cast off at and discharged through the discharging chute 15A which is slantingly formed beneath the thermostatic plate 13C.

The operation and display section 16 shown in FIG. 7 comprises a power switch 16a; a display for ion species 16b (in which "MULT" is a lamp indicating that such a multi-type slide with three pairs of the ion-selective electrodes (each for a predetermined ion species) as shown in FIG. 1 is being measured); a display for the measured ionic activity 16c; a lamp 16d for indicating the measurement ready status; a warning lamp 16e; a number keyboard 16f through which calibration data, IDs and the like are inputted; and other operation buttons 16g for various purposes; all of which are disposed on an operation panel 16A.

The measured results are printed out on a paper 17A by the printer 17. An interface for the printer 17B is disposed between said printer 17 and said panel 16A.

We claim:

1. An apparatus for measuring ionic activity comprising:
    a means for supplying slide-type ionic activity measuring devices, one by one, each said measuring device having at least one pair of ion-selective electrodes, each of which generate a potential difference corresponding to the ionic activity of one specific ion, and a porous bridge disposed between the ion-selective layers of at least one pair of said ion-selective electrodes;
    a reference spotting means for spotting a substantially predetermined contstant volume of a reference solution on one ion-selective layer of said pair of ion-selective electrodes of said measuring device;
    a sample spotting means for spotting a substantially predetermined constant volume of a sample solution on the other ion-selective layer of said pair of ion-selective electrodes of said measuring device;
    a discharging chute for discharging said measuring device;
    a first conveying means for conveying said measuring device to a measuring section after a sample solution is spotted on the other ion-selective layer of said pair of ion-selective electrodes;
    at least one pair of probes electrically connected to a means for measuring potential difference and having needle-like terminals which come into contact with said measuring device so as to measure the potential difference between said pair of ion-selective electrodes;
    a second conveying means for conveying said measuring device to said discharging chute after the measurement; and
    a cover for substantially shielding said measuring device from an ambient atmosphere;
    said first and second conveying means consisting of a turret which intermittently rotates while successively receiving said measuring devices one after the other; said turret having a plurality of measuring device receiving portions formed in the periphery of said turret at regular intervals; said reference spotting means being disposed within the rotation area of said turret in connection to a reservoir containing said reference solution and a spotting section of said measuring device, and comprising a dripping nozzle connected to said reservoir so as to drip said reference solution contained therein and a reference solution supplying means which supplies a predetermined constant volume of said reference solution from said reservoir through said nozzle when said measuring device stops below said nozzle; said pair of probes being vertically movable such that said pair of probes come into electrical contact with said pair of ion-selective electrodes so as to measure the potential difference between the ion-selective electrodes when said measuring device is motionless on said turret, and then separates from the ion-selective electrodes before said turret makes its next intermittent move; said discharging chute being formed within the rotation area of said turret so that said measuring device is automatically discharged through said discharging chute by the rotation of said turret after the measurement.

2. An apparatus for measuring ionic activity as defined in claim 1 wherein said first conveying means has a thermostatic means to maintain said measuring device at a constant temperature during motion.

3. An apparatus for measuring ionic activity as defined in claim 1 wherein said reference spotting means comprises a peristaltic pump.

4. An apparatus for measuring ionic activity as defined in claim 1 wherein said reference spotting means comprises a drip dispenser.

5. An apparatus for measuring ionic activity as defined in claim 1 wherein said pair of probes have a plurality of pairs of needle-like terminals adapted to simultaneously come into contact with a plurality of pairs of ion-selective electrodes of said measuring device.

* * * * *